United States Patent
Komatsu et al.

(10) Patent No.: US 9,119,416 B2
(45) Date of Patent: Sep. 1, 2015

(54) MUSCLE FATIGUE REMEDY

(75) Inventors: Miho Komatsu, Tsukuba (JP); Koji Morishita, Tsukuba (JP); Shin-ichi Hashimoto, Hofu (JP)

(73) Assignee: Kyowa Hakko Bio Co., Ltd., Chiyoda-ku (JP)

(*) Notice: Subject to any disclaimer, the term of this patent is extended or adjusted under 35 U.S.C. 154(b) by 959 days.

(21) Appl. No.: 12/293,722

(22) PCT Filed: Mar. 23, 2007

(86) PCT No.: PCT/JP2007/055976
§ 371 (c)(1),
(2), (4) Date: Oct. 6, 2008

(87) PCT Pub. No.: WO2007/108530
PCT Pub. Date: Sep. 27, 2007

(65) Prior Publication Data
US 2010/0168040 A1    Jul. 1, 2010

(30) Foreign Application Priority Data
Mar. 23, 2006  (JP) ................................. 2006-080972

(51) Int. Cl.
*A61K 38/05* (2006.01)
*C07K 5/06* (2006.01)
*A23L 1/305* (2006.01)

(52) U.S. Cl.
CPC ............... *A23L 1/3053* (2013.01); *A61K 38/05* (2013.01); *A23V 2002/00* (2013.01)

(58) Field of Classification Search
None
See application file for complete search history.

(56) References Cited

U.S. PATENT DOCUMENTS

| 4,687,782 A * | 8/1987 | Brantman ...................... 514/561 |
| 7,939,099 B2 * | 5/2011 | Tsuchita et al. .............. 424/439 |
| 2002/0006907 A1 * | 1/2002 | Gardiner et al. ................. 514/18 |

FOREIGN PATENT DOCUMENTS

JP    2005-97162 A    4/2005

OTHER PUBLICATIONS

Abumrad anticipates instant claims 2, 4, 5, 7 and 9.*
Website: http://1828.mshaffer.com/d/word/exercise, 4 pages, retrieved on Apr. 8, 2013.*
Website:http://www.huffingtonpost.com/2013/08/28/middle-age_n_3830194.html, 2 pages, Retrieved on Sep. 11, 2014.*
Website: http://en.wikipedia.org/wiki/Middle_age, 4 pages, Retrieved on Sep. 11, 2014.*
Website: http://www.middleage.org/definition.shtml, 2 pages, Retrieved on Sep. 15, 2014.*
Albers, 1988, Clinical Science, 75, 463-468.*
Furst, 2001, J. Nutr., 131, 2562S-2568S.*
Rogero, 2006, Nutrition, 22, 564-571.*
Abumrad, 1989, American Physiological Society, 257, E228-E234.*
Rogero, 2004, Nutrition Research, 24, 261-270.*
"Protection of Amide-Nitrogen for Peptide Synthesis. A Novel Synthesis of Peptides Containing C-Terminal Glutamine" Shiro Akabori et al., Short Communications, May 1961, p. 739.
Ala-Gln L-Alanyl-LGlutamine, Kyowa Hakko Kogyo Co., Ltd., Bio-Chemicals Business Unit, Mar. 2006 cover page, contents, p. 1-4, 43, and end.
"Studies on the Synthesis of Peptides Containing Glutamine as the C-Terminal. I. Protection of Amide-nitrogen with Xanthyl Group during Peptide Synthesis", Yasutsugu Shimonishi et al., vol. 35, No. 12, Dec. 1962, 1966-1970.
"Availability of amino acids supplied intravenously in healthy man as synthetic dipeptides: kinetic evaluation of L-alanyl-L glutamine and glycyl-L-tyrosine", S. Albers et al., Clinical Science (1988) 75, 463-468.
"Plasma and tissue glutamine response to acute and chronic supplementation with L-glutamine and L-alanyl-L-glutamine in rats", M. M. Rogero, et al., Nutrition Research 24 (2004) 261-270.
"Studies on the Synthesis of Peptides Containing C-Terminal Glutamine. II. The Synthesis and Use of α-p-Nitrobenzyl γ-Methyl L-Glutamate", Yasutsugu Shimonishi et al., vol. 37, No. 2, 1964, 200-203.
"Effect of alanyl-glutamine supplementation on plasma and tissue glutamine concentrations in rats submitted to exhaustive exercise", Rogero, M.M. et al, Nutrition, 2006, vol. 22, No. 5, p. 564-571.
Lima et al., "Effects of an Alanyl-Glutamine-Based Oral Rehydration and Nutrition Therapy Solution on Electrolyte and Water Absorption in a Rat Model of Secretory Diarrhea Induced by Cholera Toxin", Nutrition 18:458-462, 2002.
Satoh et al., "Nutritional benefits of enteral alanyl-glutamine supplementation on rat small intestinal damage induced by cyclophosphamide", Journal of Gastroenterology and Hepatology, 18, 719-725, 2003.
Matilla et al., "Effects of Parenteral Nutrition Supplemented With Glutamine or Glutamine Dipeptides on Liver Antioxidant and Detoxication Systems in Rats", Nutrition 16:125-128, 2000.

* cited by examiner

*Primary Examiner* — Satyanarayana R Gudibande
(74) *Attorney, Agent, or Firm* — Fox Rothschild LLP

(57) ABSTRACT

A muscle fatigue remedy that for persons with the symptoms of muscle pain attributed to strenuous exercise, lassitude in the arms and legs attributed to acute exercise, lower back pain and stiffness in the shoulder attributed to taking of a certain posture over a prolonged period of time, etc., relieves the symptoms and allows them to have a fulfilling life. There is provided a muscle fatigue remedy containing alanyl-glutamine or its salt as an active ingredient.

9 Claims, No Drawings

MUSCLE FATIGUE REMEDY

CROSS REFERENCE TO PRIOR RELATED APPLICATIONS

This application is a United States national phase application under 35 U.S.C. §371 of International Patent Application No. PCT/JP2007/055976, filed on Mar. 23, 2007, and claims the benefit of Japanese Patent Application No. 2006-080972, filed on Mar. 23, 2006, both of which are incorporated by reference herein. The International Application was published in Japanese on Sep. 27, 2007, as International Publication No. WO 2007/108530 A1 under PCT Article 21(2).

FIELD OF THE INVENTION

The present invention relates to a muscle fatigue remedy containing alanylglutamine or a salt thereof as an active ingredient.

BACKGROUND OF THE INVENTION

Muscle fatigue includes muscle pain attributed to strenuous exercise, lassitude in the arms and legs attributed to acute exercise, and lower back pain and stiffness in the shoulder attributed to holding of a fixed posture over a prolonged period of time.

Well-known methods to relieve muscle fatigue include massage, and nutritional supplements such as vitamins and proteins, etc.

Alanylglutamine is a dipeptide containing two amino acids, alanine and glutamine, and is immediately degraded into alanine and glutamine in the body (refer to "Clinical Science", 1988, Vol. 75, No. 5, p. 463-8). The action of glutamine is known to have many effects on physiological functions such as the regulation of skeletal muscle protein metabolism, repair of small intestine mucosa, and improvement of immunofunction, and it has been reported that the effects of alanine on physiological functions include an action to suppress blood sugar levels in diabetes patients (refer to "L-Alanyl-L-Glutamine", Kyowa Hakko Co., Ltd., 2006, p. 1).

Alanylglutamine is superior in heat stability and solubility in aqueous solutions compared to glutamine, which has low-solubility and poor stability (refer to "L-Alanyl-L-Glutamine", Kyowa Hakko Co., Ltd., 2006, p. 3), and is used in parenteral nutritional agents as a glutamine supply source.

Glutamine peptide derived from wheat gluten is known to have an action to decrease the feeling of fatigue and muscle pain after an exercise load (refer to Japanese Unexamined Patent Publication No. 2005-97162).

Nonetheless, alanylglutamine is not known to have an action to remedy muscle fatigue.

SUMMARY OF THE INVENTION

There is a demand for pharmaceutical products and nutritional foods, etc., that improve symptoms and create fulfilling lives for people having subjective symptoms of muscle pain attributed to strenuous exercise, lassitude in the arms and legs attributed to acute exercise, and lower back pain and stiffness in the shoulder attributed to holding of a fixed posture over a prolonged period of time. Specifically, an object of the present invention is to offer a muscle fatigue remedy.

The present invention includes the following aspects.

One aspect is a muscle fatigue remedy containing alanylglutamine or a salt thereof as an active ingredient.

Another aspect is a method of remedying muscle fatigue characterized in that an effective amount of alanylglutamine or a salt thereof is administered to a subject in need.

Yet another aspect is a use of alanylglutamine or a salt thereof for producing a muscle fatigue remedy.

The present invention offers a safe and effective muscle fatigue remedy that contains alanylglutamine or a salt thereof as an active ingredient.

DETAILED DESCRIPTION OF THE INVENTION

In the composition of the present invention, alanine and glutamine are the amino acids that constitute alanylglutamine. Each may be L- or D-forms respectively, and the L-forms are preferred.

Salts of alanylglutamine include acid addition salts, metal salts, ammonium salts, organic amine addition salts, amino acid addition salts, and the like.

The acid addition salts include: inorganic acid salts such as hydrochloride, hydrosulfate, nitrate and phosphate; and organic acid salts such as acetate, maleate, fumarate, citrate, malate, lactate, a-ketoglutarate, gluconate and caprylate.

The metal salts include: alkali metal salts such as sodium salt and potassium salt; alkaline earth metal salts such as magnesium salt and calcium salt; aluminum salt; zinc salt, and the like.

Ammonium salts include salts of ammonium, tetramethylammonium, and the like.

Organic amine addition salts include salts of morpholine, piperidine, and the like.

Amino acid addition salts include salts of glycine, phenylalanine, lysine, aspartic acid, glutamic acid, and the like.

Alanylglutamine may be produced according to any method such as synthetic method, enzymatic method, or fermentation method.

Methods for producing alanylglutamine include, for example, those cited in Bulletin of the Chemical Society of Japan, 34, 739 (1961), 35, 1966 (1962), 37, 200 (1964), European Patent No. 311057, German Patent No. 3206784, Japanese Unexamined Patent Publication No. H6-234715, and WO2004/058960.

Commercial products (those manufactured by Kyowa Hakko, Co., Ltd., Kokusan Kagaku, Co., Ltd., and Bachem AG, etc.) may be used for alanylglutamine.

Muscle fatigue can be remedied by administering the muscle fatigue remedy of the present invention to persons having muscle fatigue.

In the present invention, muscle fatigue means the symptoms of muscle pain attributed to strenuous exercise, lassitude in the arms and legs attributed to acute exercise, and lower back pain and stiffness in the shoulder attributed to holding of a fixed posture over a prolonged period of time.

Alanylglutamine or a salt thereof may be administered as it is as the muscle fatigue remedy of the present invention, but preferably alanylglutamine is provided in any of a variety of pharmaceutical preparations.

These pharmaceutical preparations contain alanylglutamine or a salt thereof as an active ingredient, but may also contain any other therapeutic active ingredients. Further, these pharmaceutical preparations may be produced by any method well known in the technical field of pharmaceutics by mixing active ingredients with one or more pharmaceutically acceptable carriers.

It is desirable to use the pharmaceutical preparation through a dosing route that is the most effective for the therapy, and examples thereof include oral administration and parenteral administration such as intravenous administration, intraperitoneal administration, or subcutaneous administration; but oral administration is preferred.

The dosage form may be oral preparations, such as tablets, powders, granules, pills, suspensions, emulsions, infusions/decoctions, capsules, syrups, liquid preparations, elixirs, extracts, tinctures and fluid extracts, or parenteral preparations, such as injections, drip IV, creams and suppositories; but oral preparations are preferable.

When preparing oral preparations, excipients may be used such as fillers, binders, disintegrators, lubricants, dispersing agents, suspension agents, emulsifiers, diluents, buffers, antioxidant agents, microbial inhibitors, and the like.

Liquid preparations suitable to oral administration, for example, syrups, can be formulated by adding: water; a saccharide such as sucrose, sorbitol, or fructose; a glycol such as polyethylene glycol, or propylene glycol; an oil such as sesame oil, olive oil, or soybean oil; an antiseptic such as a p-hydroxybenzoate ester; a preservative such as a paraoxybenzoate derivative like methyl paraoxybenzoate or sodium benzoate; a flavor such as strawberry flavor or peppermint; or the like.

Further, for example, tablets, powders or granules, each of which is suitable for oral administration, can be formulated by adding: a saccharide such as lactose, sugar, glucose, sucrose, mannitol, or sorbitol; a starch such as that of potato, wheat, or corn; an inorganic substance such as calcium carbonate, calcium sulfate, sodium hydrogen carbonate, or sodium chloride; a filler such as crystalline cellulose or plant powder like licorice root powder, gentian powder, or the like; a disintegrator such as starch, agar, gelatin powder, crystalline cellulose, carmellose sodium, carmellose calcium, calcium carbonate, sodium hydrogen carbonate, or sodium alginate; a lubricant such as magnesium stearate, talc, hydrogenated plant oil, macrogol, or silicone oil; a binder such as polyvinyl alcohol, hydroxypropyl cellulose, methyl cellulose, ethyl cellulose, carmellose, gelatin, or starch paste; a surfactant such as a fatty acid ester; a plasticizer such as glycerol; or the like.

Additives generally used in foods or drinks may be added to preparations suitable for oral administration, including: sweeteners, colorants, preservatives, thickening stabilizers, antioxidant agents, coloring agents, bleaching agents, antifungal agents, gum bases, bitter agents, enzymes, waxes, sour agents, seasonings, emulsifiers, reinforcing agents, manufacturing agents, flavors, spice extracts, or the like.

The preparation suitable for oral administration may be used as a food or drink for relieving muscle fatigue such as a health food, a functional food, a nutritional supplement food, or a food for specific health use; and these may be in an unprocessed form or in such forms as a powdered food, a sheet-shaped food, a bottled food, a canned food, a retort food, a capsule food, a tablet food, a liquid food, or a drinkable preparation.

Suitable parenteral administration includes, for example, an injection that preferably contains a sterilized aqueous preparation containing alanylglutamine or a salt thereof, which is isotonic to the recipient's blood. In the case of an injection, for example, a solution for injection is prepared using a carrier containing a salt solution, a glucose solution, or a mixture of a salt solution and a glucose solution, or the like.

Further, also added to these parenteral preparations may be one or more auxiliary components selected from the diluents, antiseptics, flavors, fillers disintegrators, lubricants, binders, surfactants and plasticizers described in the examples of the oral preparations, and the like.

In the muscle fatigue remedy of the present invention, the concentration of alanylglutamine or a salt thereof is appropriately selected depending on the type of preparation, the effect expected by administration of the preparation, and the like, but, for example, the concentration in the case of an oral preparation is usually 0.1 to 100% by weight as alanylglutamine or a salt thereof, preferably 0.5 to 70% by weight, and particularly preferably 1 to 50% by weight.

The dose and the administration frequency of the muscle fatigue remedy of the present invention may vary depending on the dosing form, the age and body weight of the patient, and the nature or the severity of the symptoms to be treated, but in general, it is administered once to several times a day usually in an amount of 5 mg to 10000 mg, preferably 50 mg to 5000 mg, more preferably 500 mg to 3000 mg per day for an adult in terms of alanylglutamine or a salt thereof. The dosing period is not particularly limited, but is usually for 1 day to 1 year, preferably 2 weeks to 3 months.

Test examples in which the muscle fatigue relief effect of alanylglutamine was examined are indicated below.

TEST EXAMPLE 1

Twenty-six healthy males ages 21 to 60 consumed alanylglutamine (manufactured by Kyowa Hakko Co., Ltd.) continuously for 1 month, and the muscle fatigue status of the subjects was evaluated.

The results are indicated in Table 1.

TABLE 1

| Age | Consumption timing | Amount consumed/administration | Muscle fatigue status |
| --- | --- | --- | --- |
| 51 to 55 years | Before going to bed | Approximately 0.5 g | Became less prone to fatigue |
| 41 to 45 years | Morning and evening | 0.5 g | No lingering fatigue from the day before when getting up from bed |
| 31 to 35 years | Morning and evening | 0.2 g | Reduction in the feeling of fatigue |
| 45 to 50 years | Before going to bed | Approximately 2.5 g | Reduction of stiff shoulders the following day |
| 26 to 30 years | After exercising | 1 g | Substantial relief of muscle pain the following day |
| 51 to 55 years | Every morning | 1 g | Alleviation of muscle pain after exercise |
| 31 to 35 years | Morning and before going to bed | 0.6 g | Reduction of muscle pain after exercise |
| 56 to 60 years | Morning and evening | 0.5 g | Reduction of muscle pain |
| 46 to 50 years | After meals morning and evening | 1 g | Less fatigue and muscle pain after exercise |

TABLE 1-continued

| Age | Consumption timing | Amount consumed/administration | Muscle fatigue status |
|---|---|---|---|
| 31 to 35 years | Morning | 0.5 g | Lighter muscle pain after exercise |
| 31 to 35 years | Before exercise | 8 g | Feeling of damage relief |
| 26 to 30 years | Before and after exercise | Approximately 1 g | Reduction of muscle fatigue |
| 45 to 50 years | After exercise | Approximately 2.5 g | Lighter muscle fatigue the following day |
| 21 to 25 years | Before going to bed | 2 g | Disappearance of muscle pain the day after soccer training and games |
| 36 to 40 years | Morning and evening | 0.5 g | Reduction of muscle pain |

Of the 26 subjects, relief of muscle fatigue was observed in the 15 subjects listed in Table 1, and alleviation of muscle pain after exercise occurred in 10 of the listed subjects.

The above results demonstrate the muscle fatigue relief effect of alanylglutamine. Examples of the present invention are indicated below.

EXAMPLE 1

Manufacturing of a Tablet Containing Alanylglutamine

A mixture of 136.2 kg of alanylglutamine, 36.0 kg of microcrystalline cellulose, 6.6 kg of sucrose fatty acid ester, 1.2 kg of calcium phosphate, and 20.0 kg of β-cyclodextrin are mixed using a conical blender (CB-1200 Blender, manufactured by Nihon Kansoki Co., Ltd.). The mixture obtained is compressed and molded to a tablet for muscle fatigue relief of 250 mg with 8 mm of diameter under 10 kN of compression-molding pressure using a rotary compression molding machine (VIRGO524SS1AY, manufactured by Kikusui Seisakusho Co., Ltd.).

EXAMPLE 2

Manufacturing of an Enteric Capsule Containing Alanylglutamine

A mixture of 20 kg of the mixture produced in Example 1 and 0.2 kg of silicon dioxide are mixed and agitated. The mixture obtained is put into a capsule-filling machine to fill 20,000 tablets of gelatin Number 2 hard-capsules, and hard-capsules are obtained. The surfaces of the hard-capsules are coated with a zein solution using a High Coater HCT-48 (manufactured by Freund Corporation) to produce 20,000 enteric capsules for muscle fatigue relief.

EXAMPLE 3

Manufacturing of an Enteric Tablet Containing Alanylglutamine

The surfaces of the tablets produced in Example 1 are coated with a shellac solution using a High Coater HCT-48 (manufactured by Freund Corporation) to produce enteric tablets for muscle fatigue relief.

EXAMPLE 4

Manufacturing of a Beverage Containing Alanylglutamine

An amount of 1.28 kg of alanylglutamine, 3 kg of erythritol (manufactured by Nikken Kagaku Co., Ltd.), 0.05 kg of citric acid, 3 g of artificial sweetener, and 0.06 kg of flavor are stirred and dissolved in 50 L of water at a temperature of 70° C. After the pH of the solution is adjusted to 3.3 with citric acid, the solution is sterilized using plate sterilization and filled into bottles. The bottles are sterilized using a pasteurizer, and thus a drink for muscle fatigue relief is produced.

According to the present invention, a muscle fatigue remedy containing alanylglutamine or a salt thereof as an active ingredient can be provided.

What is claimed is:

1. A method of alleviating muscle pain and muscle fatigue of healthy adults, wherein the muscle pain and muscle fatigue are result of strenuous exercise, through orally administering alanylglutamine or a salt thereof alone in the amount of 5 mg or more and 10,000 mg or less per day.

2. The method of alleviating muscle pain and muscle fatigue of healthy adults according to claim 1, wherein the alanylglutamine or salt thereof is administered alone in an amount of 50 mg or more and 5,000 mg or less per day.

3. The method of alleviating muscle pain and muscle fatigue of healthy adults according to claim 1, wherein the alanylglutamine or salt thereof is administered alone in an amount of 500 mg or more and 3,000 mg or less per day.

4. The method of alleviating muscle pain and muscle fatigue of healthy adults according to claim 1, wherein the alanylglutamine or salt thereof is administered alone for a period of 1 day or more and 1 year or less.

5. The method of alleviating muscle pain and muscle fatigue of healthy adults according to claim 1, wherein the alanylglutamine or salt thereof is administered alone for a period of 2 weeks or more and 3 months or less.

6. The method of alleviating muscle pain and muscle fatigue of healthy adults according to claim 1, wherein the alanylglutamine or a salt thereof alone in the amount of 5 mg or more and 10,000 mg or less per day is orally administered as a preparation at a concentration of 0.1% or more by weight.

7. The method of alleviating muscle pain and muscle fatigue of healthy adults according to claim 1, wherein the alanylglutamine or salt thereof alone in the amount of 5 mg or more and 10,000 mg or less per day is orally administered as a preparation at a concentration of 0.5% or more and 70% or less by weight.

8. The method of alleviating muscle pain and muscle fatigue of healthy adults according to claim 1, wherein the alanylglutamine or salt thereof alone in the amount of 5 mg or more and 10,000 mg or less per day is orally administered as a preparation at a concentration of 1% or more and 50% or less by weight.

9. The method of alleviating muscle pain and muscle fatigue of healthy adults according to claim 1, wherein the healthy adult is 33 years of age or older.

* * * * *